(12) United States Patent
Trnka

(10) Patent No.: US 6,755,838 B2
(45) Date of Patent: Jun. 29, 2004

(54) ARTHRODESIS GUIDE FOR ANGULARLY POSITIONING JOINT BONES

(75) Inventor: Hans-Jorg Trnka, Vienna (AT)

(73) Assignee: Newdeal S.A., Lyons (FR)

( * ) Notice: Subject to any disclaimer, the term of this patent is extended or adjusted under 35 U.S.C. 154(b) by 93 days.

(21) Appl. No.: 10/115,425

(22) Filed: Apr. 4, 2002

(65) Prior Publication Data

US 2002/0165551 A1 Nov. 7, 2002

(30) Foreign Application Priority Data

Apr. 4, 2001 (FR) .............................. 01 04592

(51) Int. Cl.$^7$ ................................................ A61F 5/00
(52) U.S. Cl. ...................................................... 606/86
(58) Field of Search ............................ 606/86, 53, 54, 606/56, 59, 102, 87, 62; 623/18.11, 19.11, 21.19, 23.39, 53, 54

(56) References Cited

U.S. PATENT DOCUMENTS

| 3,704,707 A | * | 12/1972 | Halloran ...................... 606/97 |
| 3,809,075 A | * | 5/1974 | Matles ......................... 606/72 |
| 3,835,849 A | | 9/1974 | McGuire |
| 4,340,059 A | * | 7/1982 | Marinoff ...................... 606/166 |
| 4,535,768 A | * | 8/1985 | Hourahane et al. ............ 606/86 |
| 4,722,331 A | | 2/1988 | Fox |
| 4,883,048 A | * | 11/1989 | Purnell et al. ................. 606/96 |
| 4,919,119 A | * | 4/1990 | Jonsson et al. ............... 606/54 |
| 4,969,909 A | * | 11/1990 | Barouk ......................... 623/21 |
| 5,645,548 A | * | 7/1997 | Augsburger ................... 606/87 |
| 5,688,284 A | * | 11/1997 | Chervitz et al. ............... 606/96 |
| 5,968,050 A | * | 10/1999 | Torrie .......................... 606/87 |
| 6,030,391 A | * | 2/2000 | Brainard et al. ............... 606/87 |
| 6,613,039 B1 | * | 9/2003 | Namba ......................... 604/541 |

FOREIGN PATENT DOCUMENTS

| EP | 0 428 452 | 5/1991 |
| FR | 910 078 | 5/1946 |

OTHER PUBLICATIONS

French Search Report from FR 0104592 dated Nov. 26, 2001.

* cited by examiner

Primary Examiner—Eduardo C. Robert
Assistant Examiner—David Comstock
(74) Attorney, Agent, or Firm—Millen, White, Zelano, Branigan, P.C.

(57) ABSTRACT

The invention provides a guide for angularly positioning bones in a joint in order to perform arthrodesis, the guide comprising:

a base for positioning on the joint, and having an adjustment shaft whose position is designed to be adjusted so as to be substantially vertically above a fixed first geometrical reference point R of the joint; and an adjustment assembly mounted to slide axially and in rotation on the adjustment shaft to adjust respectively a height for the assembly relative to the first geometrical reference point R and a first angle α for the assembly about said axis, said adjustment assembly being formed by an angular adjustable member which can be positioned on a graduated piece to adjust a second angle β centered on the first geometrical reference point R, but situated in a plane different from the first angle α.

The guide is suitable for metatarso-phalangeal positioning.

26 Claims, 2 Drawing Sheets

ARTHRODESIS GUIDE FOR ANGULARLY POSITIONING JOINT BONES

FIELD OF THE INVENTION

The present invention relates to the general technical field of appliances for assisting in angularly positioning the bones of a joint in order to perform arthrodesis.

The present invention provides a guide for angularly positioning the bones of a joint in order to perform arthrodesis.

In a preferred but non-exclusive application, the angular positioning guide in accordance with the invention is more particularly intended and designed for angularly positioning the metatarso-phalangeal joint, it being understood that applications to other joints, and in particular those of the shoulder, can also be envisaged.

BACKGROUND OF THE INVENTION

In cases of arthrosis occurring in bone joints, and in particular in the metatarso-phalangeal joint, it is often necessary to perform arthrodesis in order to fuse the two bones together. In general, arthrodesis is a difficult operation since it locks a joint in a defined position in irreversible manner. Thus, arthrodesis of the metatarso-phalangeal joint is of very great importance insofar as this joint is involved in critical manner in the walking cycle of a human being. It will thus be understood that it is essential for the two bones to be positioned relative to each other prior to being fused in an orientation with the best possible accuracy in order to avoid any subsequent impediment.

It is therefore essential to fix the relative axes of the bones so as to comply as well as possible with the flexions and the axes of the patient, and do this as a function of the patient's sex and morphology.

Until now, metatarso-phalangeal arthrodeses have been performed in relatively empirical manner, with the values for the angles between the metatarsus and the phalanges being determined and fixed in relatively crude manner, with respect to determining both the varus-valgus angle and the dorsiflexion angle of the joint.

In practice, it is found that if the angles selected by the surgeon are poorly complied with during the operation, consequently leading to an incorrect fixing of the fusion axes between the bone, then either the patient is impeded when walking, with the patient consequently compensating by corrective positioning that can itself give rise to secondary troubles, or else the patient has difficulty in putting on and taking off shoes, or indeed suffers from rubbing or irritations that give rise to various sores.

In all cases, failure to comply with fusion angles carefully determined in advance by the surgeon gives rise to consequences that are harmful for the patient who has been subjected to arthrodesis, and these consequences need to be avoided.

OBJECTS AND SUMMARY OF THE INVENTION

A particular object of the invention is to remedy the various drawbacks listed above, and to propose an appliance or guide for angularly positioning the bones of a joint in order to perform arthrodesis.

Another object of the invention is to propose a positioning guide that is particularly adapted to angularly position the metatarso-phalangeal joint in a manner that is simple and reliable.

Another object of the invention is to propose a positioning guide whose initial adjustment and installation are particularly easy.

Another object of the invention is to propose a positioning guide enabling the various axes to be adjusted in a manner that is quick and reliable.

Upon further study of the specification and appended claims, further objects and advantages of this invention will become apparent to those skilled into the art.

These objects given to the invention are achieved by means of a guide for angularly positioning the bones of a joint for the purpose of performing arthrodesis and comprising:

a base for positioning on the joint, and having an adjustment shaft whose position is designed to be adjusted so as to be substantially vertically above a fixed first geometrical reference point of the joint; and an adjustment assembly mounted to slide axially and in rotation on the adjustment shaft to adjust respectively a height for the assembly relative to the first geometrical reference point and a first angle $\alpha$ for the assembly about said axis, said adjustment assembly being formed by an angular adjustable member which can be positioned on a graduated piece to adjust a second angle $\beta$ centered on the first geometrical reference point, but situated in a plane different from the first angle $\alpha$.

BRIEF DESCRIPTION OF THE DRAWINGS

Other advantages and objects of the invention will appear in greater detail on reading the following description and from the accompanying drawings provided purely by way of non-limiting explanation, and in which.

MORE DETAILED DESCRIPTION

Figure 1:
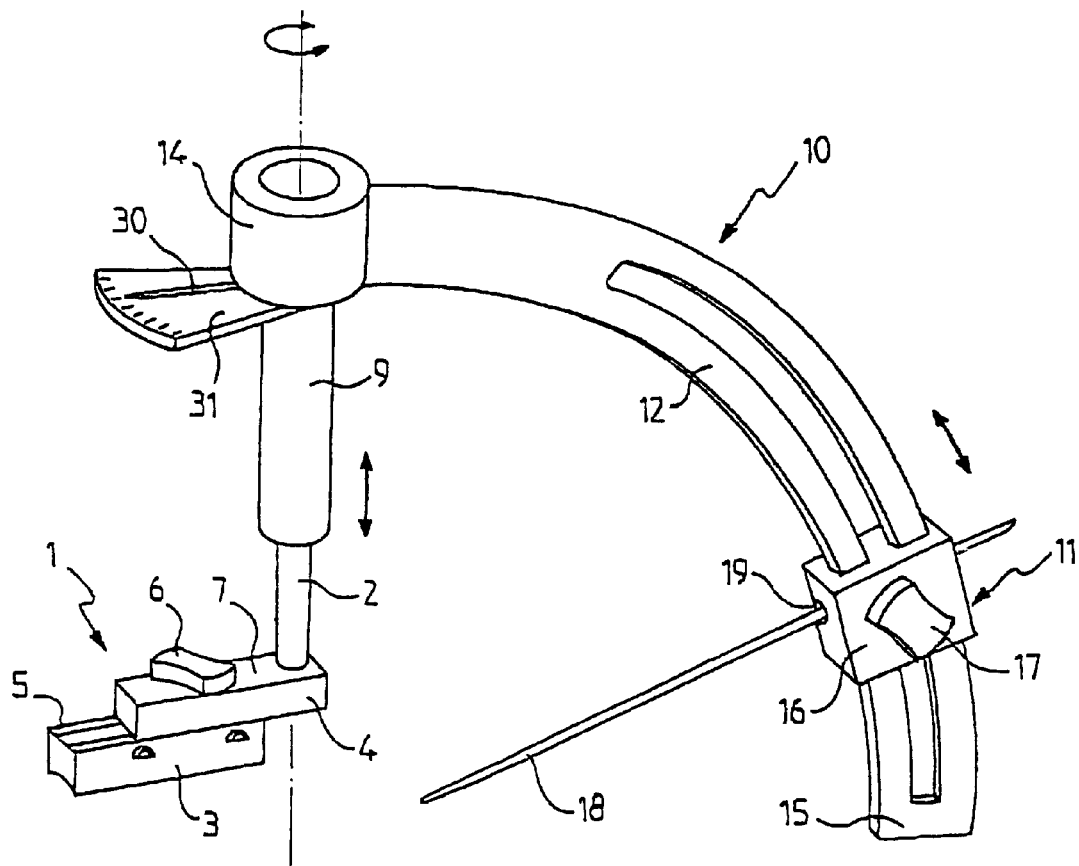
FIG. 1 is a general perspective view of the guide of the invention for angularly positioning the bones of a joint.
Figure 3:
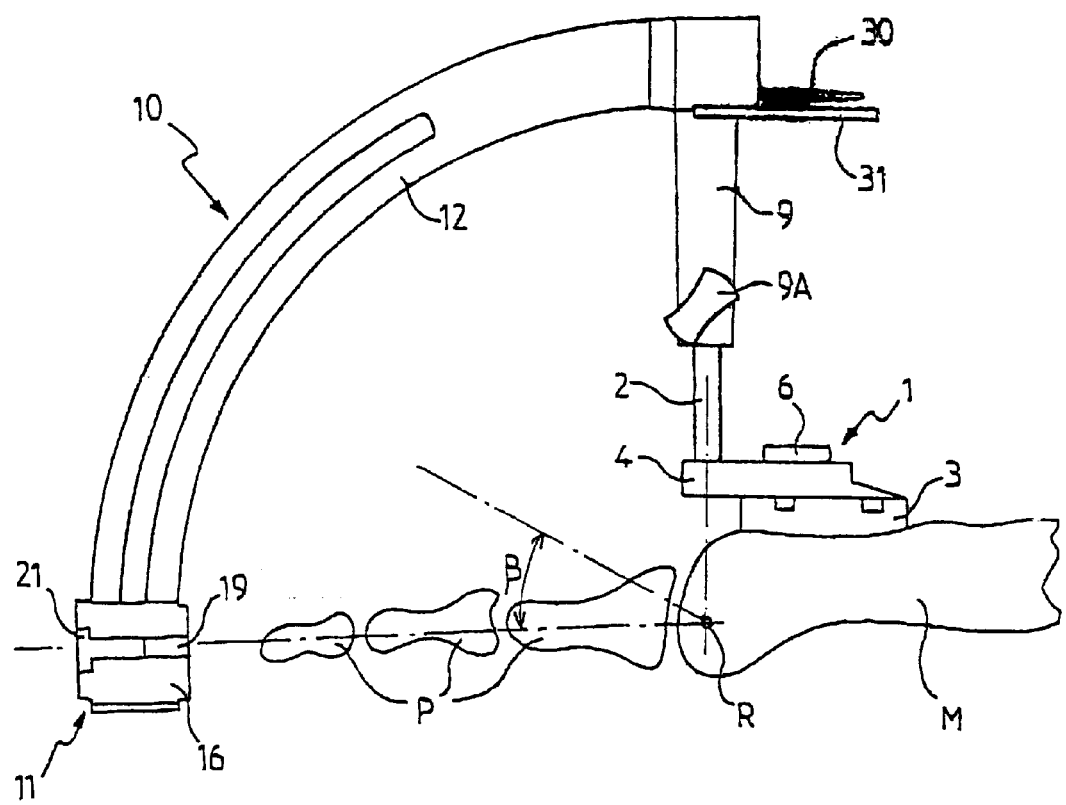
FIG. 3 is a side view showing how the dorsiflexion angle of a metatarso-phalangeal joint is adjusted.

The appliance or guide for angularly positioning the bones of a joint in order to perform arthrodesis and corresponding to the invention is shown in FIGS. 1 and 3 and is intended more particularly to perform angular positioning of the metatarso-phalangeal joint of a human being.

Nevertheless, it will be understood that applications to angularly positioning the bones of some other joint can be envisaged, and that is why the novel appliance described should not be restricted in any way to arthrodesis of the metatarso-phalangeal joint, even though for the needs of describing the present patent application, it is an application to this specific joint that is described.

Thus, as shown in the figures, the angular positioning guide comprises a base 1 for being positioned on a joint, and specifically it is shown on the metatarsus M of the metatarso-phalangeal joint. The base 1 includes an adjustment shaft 2 extending substantially vertically when the base 1 is put into place on the metatarsus M and whose position is designed to be adjusted so as to be substantially vertical over a fixed first geometrical reference point R of the joint.

As shown, and in its preferred application to a metatarso-phalangeal joint, the fixed first geometrical reference point R is the center of rotation of the joint head of the metatarsus M.

Figure 2:
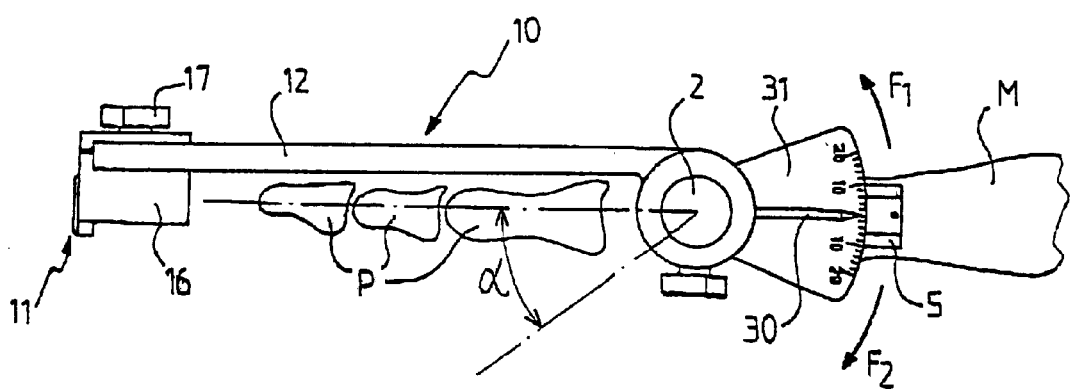
FIG. 2 is a plan view showing how the varus-valgus angle is adjusted for arthrodesis of the metatarso-phalangeal joint.

In the preferred variant shown in FIGS. 1 to 3, the base is advantageously formed by a main plate 3 provided with fixing means (not shown in the figures), for example through orifices to enable screws to be inserted for fixing it securely to a bone of the joint. In this preferred variant, the base 1 is also formed by a secondary plate 4 movably mounted on the main plate 3, said secondary plate 4 supporting the adjustment shaft 2 so as to be able to adjust the position of said shaft relative to the center of rotation R of the metatarsus M.

The secondary plate 4 can be movably mounted on the main plate 3 by any technical means well known to the person skilled in the art, for example by means of a slideway mount 5 associated with a locking member 6 such as a rotary knob.

In this manner, after initially fixing the main plate 3 on the metatarsus M, the surgeon can easily and quickly bring the adjustment shaft 2 over the geometrical reference point R merely by sliding the secondary plate 4. Once this movement has been performed, the secondary plate 4 is locked in position by means of the adjustment knob 6.

Naturally, in a variant, it is quite possible to envisage making the device of the invention with a base 1 having a single plate, the operation of positioning the adjustment shaft 2 then being more difficult for the surgeon to perform since it is then associated with said base being positioned and fixed simultaneously.

In the examples shown, the main plate 3 and the secondary plate 4 are made in the form of pieces that are substantially in the form of rectangular parallelepipeds, defining respective substantially plane sliding faces, the secondary plate 4 having a top face 7 from which the adjustment shaft 2 extends substantially perpendicularly to the plane in which said face 7 extends.

The angular positioning guide of the invention also has an adjustment assembly 10 mounted to slide axially and to turn on the adjustment shaft 2, respectively to adjust a height for said assembly 10 relative to the fixed first geometrical reference R, and to adjust a first angle $\alpha$ for said assembly about said shaft 2.

Advantageously, the adjustment assembly 10 comprises a hollow tubular sleeve 9 provided with a locking screw 9A, said sleeve being engaged on or in the shaft 2 (FIG. 3). The shaft can be provided with a flat to facilitate locking in rotation.

In an application to a metatarso-phalangeal joint, rotating the adjustment assembly 10 serves to adjust the varus-valgus angle which will thus correspond to an angle $\alpha$. This adjustment can be performed by means of a pointer 30 and a graduated plate 31, one being connected to the shaft 2 and the other to the sleeve 9 or to the adjustment assembly 10, for example.

In this disposition, the adjustment assembly 10 includes an angular adjustment member 11 which can be positioned on a graduated piece 12 to adjust a second angle $\beta$ centered on the fixed first geometrical reference point R, but situated in a plane that is different from the first angle $\alpha$.

For a metatarso-phalangeal joint, the guide of the invention is made in such a manner that the adjustment axis 2 is perpendicular to the plane in which the base 1 extends, and the adjustment member 11 together with the graduated piece 12 are arranged to adjust the second angle $\beta$ in a plane which is perpendicular to that in which the first angle $\alpha$ is adjusted.

Thus, the guide of the invention makes it possible to define a reference center R relative to which a complete geometrical reference system is adjusted, i.e. by means of the adjustment shaft 2, a reference plane, and then in said plane a first angle $\alpha$ turning about the adjustment shaft 2, and then a second angle $\beta$ by moving and positioning the adjustment member 11. This obtains a preferably orthonormal geometrical frame of reference that is complete.

As shown in the figures, the adjustment assembly 10 is mounted on the adjustment shaft 2 by means of the graduated piece 12 which is rotatably supported on the adjustment shaft 2 via one of its ends 14 extended by the sleeve 9.

Advantageously, the graduated piece 12 is formed by a ruler in the form of one-fourth of a circle extending in a plane perpendicular to the plane in which the base 1 extends, the free end 15 of the ruler being situated at a level that is lower than the assembly end 14 on the adjustment shaft 2. This thus makes it possible for the angle $\beta$ to be adjusted angularly through an amplitude of 45°.

As shown in the figures, the angular adjustment member 11 has a slider 16 which is movably mounted on the graduated piece 12 provided with a slot formed in the thickness of said piece. The slider 16 is associated with a locking and unlocking member 17 mounted on said slider 16, and adapted to be handled by the surgeon, serving to move and then fix the angular position of the slider 16.

The slider 16 is adapted to support a surgical pin 18 which is suitable for being threaded axially through the various bones forming the phalanges of the joint (FIG. 2) in order to perform arthrodesis.

In order to adjust the angle $\beta$ corresponding to the dorsiflexion angle of the metatarso-phalangeal joint, the surgeon must begin by aligning all of the bones of the joint axially using the surgical pin 18 which is initially threaded through the bones. Thereafter the surgeon must fix the desired dorsiflexion angle in three dimensions so as to perform arthrodesis itself, which implies that the surgeon must have available a fixed support for holding the surgical pin 18 at the selected value for the angle $\beta$.

To perform this support function, the slider 16 is provided on one of its faces with a groove 19, e.g. of semicircular shape, and of a size that is sufficient to be able to hold a portion of the length of the surgical pin 18 in stable manner while still enabling the pin 18 to be inserted laterally after it has previously been threaded through the phalanges.

Advantageously, in order to facilitate insertion and in order to improve stable support of the surgical pin 18 in the groove 19, a centralizer 20 is provided (FIGS. 3 and 4) for being threaded and locked in position on the free end of the pin 18 after it has been inserted through the phalanges. For this purpose, the groove 19 presents a specific cutout of suitable shape and dimensions corresponding to those of the centralizer 20, thus enabling the centralizer to be inserted into the groove so as to be supported stably in said housing 21.

Figure 4:
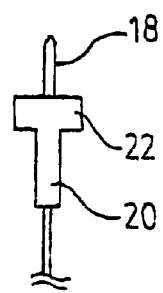
FIG. 4 is a detail side view showing a centering element used with a positioning guide of the invention.

As shown in FIGS. 3 and 4, the centralizer is in the form of a small cylindrical piece having a longitudinal insertion channel, said cylindrical piece being surmounted by a head of greater dimensions forming a collar 22. The housing 21 (FIG. 3) is identical in shape and corresponds to the centralizer 20 as defined in this way.

The guide for metatarso-phalangeal positioning of the invention operates on the following principle.

After an incision has been made in the metatarso-phalangeal joint, the surgeon begins by putting a surgical pin 18 into place by threading it through all of the phalanges P, as shown in part in FIG. 3. In conventional manner, the surgical pin is put into place using a motor, for example, going from the joint face towards the outside so that the point of the surgical pin 18 is flush with the joint surface. The surgeon can then immediately or subsequently insert the centralizer 20 axially and lock it in position at the free end of the surgical pin 18.

Thereafter, the surgeon positions the guide of the invention by positioning the base 1 on the top face of the metatarsus M. For this purpose, the main plate 3 is positioned and fixed, e.g. by means of pins, screws, or fixing clamps, substantially towards the end of the metatarsus M. Thereafter, the surgeon unlocks the knob 6 to allow the secondary plate 4 to move in translation and to adjust the relative position of the adjustment shaft 2 relative to the center of rotation of the metatarsus M, so that the adjustment shaft 2 lies vertically thereover. Thereafter, the adjustment shaft 2 is locked in position by turning the knob 6. This first adjustment thus corresponds to translation parallel to the main axis of the metatarsus.

Thereafter, the surgeon positions the adjustment assembly 10 which is then engaged on the adjustment shaft 2 which then needs to be adjusted in vertical position along the adjustment shaft 2. Vertical translation is continued until the surgeon positions the reference position O of the slider 16 corresponding substantially to the end 15 of the graduated piece 12 at the same height as the center of rotation R of the joint head of the metatarsus M (FIG. 3). Once this reference position has been achieved, the adjustment assembly 10 is locked in position by acting on the locking knob associated with the shaft 2.

After performing these two adjustments in translation, the surgeon is then certain that all of the angular adjustments that are performed subsequently will be about a center that coincides with the center of rotation of the metatarsus R which thus forms the fixed first geometrical reference point of the joint.

Thereafter, depending on the morphology of the patient and depending on whether the patient is a man or a woman, the practitioner adjusts the two required angular positions $\alpha$ and $\beta$ so as to perform arthrodesis on the metatarso-phalangeal joint, beginning with the varus-valgus angle (internal angle) and then continuing with the dorsiflexion angle. In general, the varus-valgus angle is adjusted to have a value $\alpha$ of about 15° to 25°, while the dorsiflexion angle is adjusted to have a value $\beta$ of about 20° to 30°.

The varus-valgus angle is then adjusted by pivoting the adjustment assembly 10 about the adjustment shaft 2 along one or other of the arrows F1 and F2 shown in FIG. 2 depending on whether the operation is performed on the patient's right side or left side. The desired varus-valgus angle is obtained by identifying the position of the pointer 30 on the graduated plate 31 (FIG. 2) where angles are marked. After reaching the desired value $\alpha$ for the varus-valgus angle, the surgeon locks the adjustment assembly 10 again on the adjustment shaft 2.

The angle $\beta$ corresponding to the dorsiflexion angle is then adjusted using the slider 16, which is brought into position on the graduated face 12 facing the desired angle, the cursor 16 then again locked in position at the desired angle $\beta$.

The practitioner can then position the pin 18 in the groove 19 by inserting the centralizer in the housing 21, thus fixing the relative position in three dimensions of the bones of the metatarso-phalangeal joint in which arthrodesis is to be performed.

In this manner, the bones of the joint are positioned in accurately fixed manner, and all that remains to be done is for the surgeon to insert the surgical pin 18 into the head of the metatarsus so as subsequently to fuse the two bony portions together. Thereafter, the surgeon can remove the guide of the invention, leaving only the surgical pin 18 in place.

The entire disclosure if all applications, patents, and publications, cited above and below, and corresponding French Application No. 01-04592, filed Apr. 4, 2001 is hereby incorporated by reference.

From the foregoing description, one skilled in the art can easily ascertain the essential characteristics of this invention and, without departing from the spirit and scope of thereof, can make various changes and modifications of the invention to adapt it to various uses and conditions.

What is claimed is:

1. A guide for angularly positioning the bones of a joint, suitable for performing arthrodesis, the guide comprising:
   a base for positioning on the joint, and having an adjustment shaft whose position is adjustable to be substantially vertically above a fixed first geometrical reference point R of the joint; and
   an adjustment assembly mounted to slide axially and in rotation on the adjustment shaft to adjust respectively a height for the assembly relative to the first geometrical reference point R and a first angle $\alpha$ for the assembly about said shaft, said adjustment assembly being formed by an angular adjustable member which is positioned on a graduated piece to adjust a second angle $\beta$ centered on the first geometrical reference point R, but situated in a plane different from the first angle $\alpha$.

2. A guide according to claim 1, wherein the adjustment shaft is perpendicular to the plane in which the base extends, and the angular adjustment member and the graduated piece are arranged to adjust the second angle $\beta$ in a plane perpendicular to that in which the first angle $\alpha$ is adjusted.

3. A guide according to claim 2, wherein the base is formed by a main plate provided with fixing means to be permanently fixed on a bone of the joint, and by a secondary plate mounted to move on the main plate and supporting the adjustment shaft so as to be able to adjust the position of said shaft.

4. A guide according to claim 3, wherein the adjustment assembly is mounted on the adjustment shaft via the graduated piece rotatably supported on the shaft at one of the ends of said shaft.

5. A guide according to claim 4, wherein the graduated piece is formed by a ruler constituting one-fourth of a circle, extending in a plane perpendicular to the plane in which the base extends, the free end of the ruler being situated at a level that is lower than the end of the mount.

6. A guide according to claim 1, wherein the base is formed by a main plate provided with fixing means to be permanently fixed on a bone of the joint, and by a secondary plate mounted to move on the main plate and supporting the adjustment shaft so as to be able to adjust the position of said shaft.

7. A guide according to claim 1, wherein the adjustment assembly is mounted on the adjustment shaft via the graduated piece rotatably supported on the shaft at one of the ends of said shaft.

8. A guide according to claim 7, wherein the graduated piece is formed by a ruler constituting one-fourth of a circle, extending in a plane perpendicular to the plane in which the base extends, the free end of the ruler being situated at a level that is lower than the end of the mount.

9. A guide according to claim 1, wherein the angular adjustment member is a movable slider.

10. A guide according to claim 9, wherein the movable slider is adapted to support a surgical pin.

11. A guide according to claim 10, wherein the slider is provided with a groove enabling the pin to be inserted laterally and to be supported.

12. A guide according to claim 11, further comprising a centralizer for threading on and locking the position of a surgical pin, and for being inserted in the groove so as to be supported in a housing formed in the slider.

13. A guide according to claim 12, wherein the adjustment shaft is perpendicular to the plane in which the base extends, and the angular adjustment member and the graduated piece are arranged to adjust the second angle β in a plane perpendicular to that in which the first angle α is adjusted.

14. A guide according to claim 13, wherein the base is formed by a main plate provided with fixing means to be permanently fixed on a bone of the joint, and by a secondary plate mounted to move on the main plate and supporting the adjustment shaft so as to be able to adjust the position of said shaft.

15. A guide according to claim 14, wherein the adjustment assembly is mounted on the adjustment shaft via the graduated piece rotatably supported on the shaft at one of the ends of said shaft.

16. A guide according to claim 15, wherein the graduated piece is formed by a ruler constituting one-fourth of a circle, extending in a plane perpendicular to the plane in which the base extends, the free end of the ruler being situated at a level that is lower than the end of the mount.

17. A guide according to claim 1, wherein the base is formed by a main plate provided with fixing means to be fixed on a bone of the joint, and by a secondary plate mounted to move on the main plate and supporting the adjustment shaft so as to be able to adjust the position of said shaft.

18. A method for positioning the bones of a joint for performing arthodesis, said method comprising:
  positioning the base of a guide according to claim 1 on a joint,
  adjusting the adjustment shaft of said guide to be substantially vertically above a fixed first geometrical reference point R of the joint; and
  adjusting the height, first angle α, and second angle β of the adjustment assembly,
  wherein before adjusting second angle β, the bones of the joint are aligned axially by threading a surgical pin through the bones.

19. A method according to claim 18, wherein the adjustment shaft is adjusted to be perpendicular to the plane in which the base extends, and the angular adjustment member and the graduated piece are arranged to adjust the second angle β in a plane perpendicular to that in which the first angle α is adjusted.

20. A method according to claim 18, wherein the adjustment assembly is mounted on the adjustment shaft via the graduated piece rotatably supported on the shaft at one of the ends of said shaft.

21. A method according to claim 18 wherein the angular adjustment member is a movable slider having a grove and a surgical pin is inserted laterally into said grove.

22. A method according to claim 21, further comprising threading a centralizer on said surgical pin, and inserting said centralizer in said groove.

23. A method according to claim 18, wherein said joint is the metatarso-phalangeal joint.

24. A method for positioning the bones of a joint for performing arthodesis, said method comprising:
  axially aligning the bones of a joint by threading a surgical pin through said bones,
  positioning the base of a guide according to claim 1 on said joint, wherein the base of said guide has a main plate which is fixed to a bone of the joint, and a movable secondary plate for adjusting the position of the adjustment shaft,
  adjusting the adjusting shaft by movement of the secondary plate so that the adjustment shaft aligns vertically over a reference point R of said joint and then locking the adjustment shaft into position,
  sliding the adjustment assembly on the adjustment shaft so that the end of the graduated piece of the adjustment assembly is at the height of reference point R,
  connecting said surgical pin to said angular adjustable member,
  pivoting the adjustment assembly about said adjustment shaft through a desired first angle α, and then locking the adjustment assembly on said adjustment shaft,
  adjusting the position of said angular adjustment member slidable on said graduated piece to a desired second angle β and then locking the angular position of the angular adjustable member thereby fixing the relative position of the bones of said joint in three dimensions.

25. A method according to claim 24, wherein said joint is the metatarso-phalangeal joint.

26. A guide for angularly positioning the bones of a joint such as the metatarso-phalangeal joint in particular, for the purpose of performing arthrodesis, the guide comprising:
  a base for positioning on the joint, and having an adjustment shaft whose position is adjustable to be substantially vertically above a fixed first geometrical reference point R of the joint; and
  an adjustment assembly mounted to slide axially and in rotation on the adjustment shaft to adjust respectively a height for the assembly relative to the first geometrical reference point R and a first angle α for the assembly about said shaft, said adjustment assembly comprising a moveable angular adjustable member to adjust a second angle β centered on the first geometrical reference point R, but situated in a plane different from the first angle α.

* * * * *

UNITED STATES PATENT AND TRADEMARK OFFICE
CERTIFICATE OF CORRECTION

PATENT NO.   : 6,755,838 B2
DATED        : June 29, 2004
INVENTOR(S)  : Trnka

Page 1 of 1

It is certified that error appears in the above-identified patent and that said Letters Patent is hereby corrected as shown below:

Column 6,
Line 36, reads "A guide according to claim 2"; it should read -- A guide according to claim 1 --
Line 42, reads "A guide according to claim 3"; it should read -- A guide according to claim 1 --

Signed and Sealed this

Fifth Day of April, 2005

JON W. DUDAS
*Director of the United States Patent and Trademark Office*